US00PP22401P2

(12) United States Plant Patent
Kordes

(10) Patent No.: US PP22,401 P2
(45) Date of Patent: Dec. 27, 2011

(54) FLORIBUNDA ROSE PLANT NAMED 'KORFREE-0006'

(50) Latin Name: *Rosa hybrida*
Varietal Denomination: KORfree-0006

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 25 days.

(21) Appl. No.: 12/799,773

(22) Filed: Apr. 30, 2010

(51) Int. Cl.
*A01H 5/00* (2006.01)

(52) U.S. Cl. ..... Plt./147

(58) Field of Classification Search ..... Plt./147, Plt./148, 149, 150
See application file for complete search history.

*Primary Examiner* — Susan McCormick Ewoldt

(57) ABSTRACT

A new and distinct variety of rose with long lasting, novel peach colored flowers, and attractive foliage with good disease resistance. It exhibits upright growth with abundant flowers. The new variety propagates well by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORfree-0006'.

CROSS REFERENCES AND FEDERAL R&D STATEMENT

There are no cross referenced or related applications. This variety was developed without the aid of any research grant.

BACKGROUND OF THE INVENTION

The present discovery constitutes a new and distinct variety of a floribunda rose which was discovered in a cultivated area in May, 2002. The new rose variety resulted from a naturally occurring mutation of unknown causation on a branch of 'KORtonetec', a non-patented rose plant.

The new rose plant was asexually propagated for further evaluation. This new and distinctive FLORIBUNDA rose variety is named 'KORfree-0006'.

SUMMARY OF THE INVENTION

The new rose plant may be distinguished from 'KORtonetec' by the following combination of characteristics:

1. 'KORtonetec' has bicolor, red and yellow flowers, while 'KORfree-0006' has peach colored flowers.

The objective of the hybridization was to create a new and distinct rose plant with unique qualities, such as:

1. Uniform growth and flowering;
2. Abundant, attractive, recurrent peach-colored flowers;
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORfree-0006' from all other varieties of which we are aware.

As part of a rose development program, Tim-Hermann Kordes asexually propagated the mutation by grafting and conducted evaluations and observations on the resulting plants in a controlled environment in Offenseth-Sparrieshoop, Germany. The resulting plants exhibited distinctive physical and biological characteristics. The first asexual reproduction of 'KORfree-0006' was done by grafting in July, 2003 at the inventor's nursery in Offenseth-Sparrieshoop, Germany.

This initial and other subsequent propagations conducted in controlled environments demonstrate that 'KORfree-0006' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, flowers, leaves, and stems of 'KORfree-0006'.

DETAILED BOTANICAL DESCRIPTION

The following is a description of 'KORfree-0006', as observed growing in October, 2009, in a nursery in Jackson County, Oreg., on plants of 3 years of age. Color references are made using The Royal Horticultural Society (London, England) Colour Chart, 2001 except where common terms of color are used.

For a comparison, several physical characteristics of the rose variety 'KORtonetec', a rose variety from the same inventor are compared to 'KORfree-0006' in Chart 1.

CHART 1

| Characteristic | 'KORfree-0006' | 'KORtonetec' |
|---|---|---|
| Petal Color-Inner Side, Middle Zone | Yellow Group 6C | Yellow-Orange Group 21B |
| Petal Color-Inner Side, Marginal Zone | Red Group 48C | Red Group 43B |
| Petal Color-Outer Side, Marginal Zone | Red Group 47D | Red Group 43A |

CHART 1-continued

| Characteristic | 'KORfree-0006' | 'KORtonetec' |
|---|---|---|
| Petal Color-Outer Side, Middle Zone | Red Group 37A | Yellow-Orange Group 21C |

Parent: 'KORtonetec'

Classification:

*Botanical classification.*—*Rosa hybrida,* 'KORfree-0006'

*Commercial classification.*—FLORIBUNDA rose.

FLOWER AND FLOWER BUD

*Blooming habit.*—Recurrent.

*Flower bud.*—Size: Upon opening, 40 mm in length from base of receptacle to end of bud and 30 mm diameter at its widest point. Bud form: Short. Pointed ovoid. Bud color: As sepals first unfold, bud color is Red Group 53D. When ¼ open, the upper surface of petals is Red Group 54B, and the lower surface is Red Group 54B. Sepals: Size: Average 20 mm long×10 mm wide. Shape: Sepals generally subulate. Sepal apex is generally cirrose. Weak foliaceous appendages on three of the five sepals. Base is flat at union with receptacle. Quantity: Five. Margins: With fine hairs and stipitate glands. Surface texture: Inner side: Pubescent. Outer surface: Mostly smooth with slight pubescence. Stipitate glands are absent. Color: Upper surface: Green Group 138B. Lower surface: Green Group 137C.

*Receptacle.*—Surface: With fine hairs. Color: Gray-Red Group 182B. Shape: Funnel. Size: 7 mm (h)×9 mm (w).

*Peduncle.*—Surface: With fine hairs and stipitate glands. Length: 65 mm average length. Diameter: 5 mm average diameter. Color: Yellow-Green Group 146B with intonations of Gray-Red Group 182B. Strength: Moderate. Borne: Multiple flower buds per stem, generally 4 to 20.

*Flower bloom.*—

*Fragrance.*—None.

*Duration.*—On the plant 16 days. As a cut flower, 8 to 12 days. Senesced petals drop away cleanly.

*Size.*—Small flowers. When open, the average flower diameter is 70 mm and the average flower height is 30 mm.

*Form.*—Shape of flower when viewed from the side: Upon opening, upper part: Flattened convex. Upon opening, lower part: Flat. Open flower, upper part: Flattened convex. Open flower, lower part: Flat.

Color:

*Upon opening, petals.*—Outermost petals: Outer Side: Marginal Zone: Red Group 47D. Middle Zone: Red Group 37A. Basal Zone: Yellow Group 11C. Inner Side: Marginal Zone: Red Group 48C. Middle Zone: Red Group 37A. Basal Zone: Yellow Group 11C. Innermost petals: Outer Side: Marginal Zone: Red Group 48C. Middle Zone: Yellow Group 6C. Basal Zone: Yellow Group 12C. Inner Side: Marginal Zone: Red Group 48C. Middle Zone: Yellow Group 6C. Basal Zone: Yellow Group 12C.

*Upon opening, basal petal spots.*—Basal petal spot, outermost petals: Small basal petal spot present on both sides. Outer Side: Yellow Group 11A. Inner Side: Yellow Group 11A. Basal petal spot, innermost petals: Small basal petal spot present on both sides. Outer Side: Yellow Group 12B. Inner Side: Yellow Group 12A.

*After opening, petals.*—Outermost petals: Outer Side: Marginal Zone: Red Group 54A. Middle Zone: Red Group 54C. Basal Zone: Yellow Group 1C. Inner Side: Marginal Zone: Red Group 54C. Middle Zone: Red Group 54C. Basal Zone: Yellow Group 1C. Innermost petals: Outer Side: Marginal Zone: Red Group 54B. Middle Zone: Red Group 54C. Basal Zone: Yellow Group 2C. Inner Side: Marginal Zone: Red Group 55B. Middle Zone: Red Group 54C. Basal Zone: Yellow Group 1B.

*After opening, basal petal spots.*—Basal petal spot, outermost petals: Outer Side: Yellow Group 1B. Inner Side: Yellow-Green Group 150C. Basal petal spot, innermost petals: Outer Side: Yellow Group 2B. Inner Side: Yellow Group 2C. Variegations: None.

General tonality: On open flower: Red Group 52B. No change in the general tonality at the end of the 10th day. Afterwards, general tonality is Red Group 52C.

Petals:

*Petal count.*—Approximately 24 petals under normal conditions.

*Petal reflex: Petals reflex slightly.*

*Petal edge: Ruffled.*

Petal shape: Rounded. Apex shape is round. Shape of base is acute.

*Petal size.*—35 mm long; 30 mm wide.

*Thickness.*—Above average.

*Petal arrangement.*—Generally in a regular pattern with overlapping edges.

Petaloids: Present.

*Petaloid count.*—Average of 6-10 per flower.

*Petaloid edge.*—Undulated.

*Petaloid texture.*—Ruffled.

*Petaloid shape.*—Spatulate.

*Petaloid size.*—Petaloids are approximately 22 mm long and 11 mm wide.

*Petaloid color.*—Color of inner side is Red Group 48D. Color of outer side is Red Group 48C.

Reproductive organs:

*Pistils.*—Approximately 50 present. Stigmas: Location: Slightly inferior in position to anthers. Color: Green-Yellow Group 160A. Styles: Length: 6 mm long. Color: Yellow-White Group 158D.

*Stamens.*—Approximately 75-90 on average and regularly arranged. Anthers: Size: 1.5 mm long. Color: Yellow-Orange Group 14C. Pollen: Generally present. Color: Yellow-Orange Group 14B. Filaments: Color: Yellow Group 13B. Length: 7 mm.

THE PLANT

*Plant growth.*—Moderate vigor. Upright to bushy habit. When grown as a budded nursery plant the average plant height is 120 cm and the average plant width is 60 cm.

*Stems.*—Stem color: Young wood: Yellow-Green Group 146C. Older wood: Yellow-Green Group 146A. Stem surface: Young wood: Smooth. Older wood: Smooth.

*Prickles.*—Present. Incidence: 15 per 10 cm of older stem. Juvenile growth without prickles. Size: Average length: 7 mm. Color: Juvenile prickles: Gray-Red Group 182 C. Mature prickles: Gray-Green Group 182C. Senescing to Yellow-Green Group 146D. Shape: Concave. Anthocyanin: Present. Color: Gray-Red Group 182 C.

*Leaves and leaflets.*—Normally 5 leaflets on normal leaves in middle of the stem. Venation pattern: Pyramidal net pattern. Leaf size: 110 mm (1)×75 mm (w). Quantity: Abundant. Texture: Upper side of leaflet: Semi glossy. Smooth. Under side of leaflet: Matte. Rough. Moderately thick. Color, mature foliage: Upper Leaf Surface: Green Group 135A. Lower Leaf Surface: Yellow-Green Group 146B. Color, juvenile foliage: Upper Leaf Surface: Green Group 143A. Lower Leaf Surface: Green Group 143B. Anthocyanin intonation: Present. Location: Intonations present on juvenile leaf margins, developing leaves, peduncles, stems.

*Stipules.*—Size: 15 mm long. 7 mm between the tips of the stipule. Main body of stipule 1.5 mm in width. Shape: Elongated, narrow. Stipule color: Yellow-Green Group 144A. Presence of stipitate glands: Present on margins. Margins: With stipitate glands.

*Petiole.*—Length: 30 mm. Diameter: 2 mm. Petiole color: Yellow-Green Group 144A. Anthocyanin present on juvenile tissue. Color: Gray-Red Group 182B. Underneath: Smooth. Stipitate glands: Limited numbers of stipitate glands on margins.

*Petiole rachis.*—Length: 35 mm. Diameter: 1.5 mm. Color: Yellow-Green Group 144A. Anthocyanin present on juvenile tissue. Margins: Entire. Prickles: A few small prickles underneath. Stipitate glands: Stipitate glands present on margins.

*Leaflets.*—Size: Average size of the terminal leaflet is 50 mm (1)×35 mm (w). Shape: Ovate. Base: Ovate. Apex: Acute. Margins: Finely serrated. Texture: Thin.

Hips/seed formation: None observed.

Winter hardiness: To date, the variety has been grown successfully in Zone 5.

Disease resistance: Above average resistance to Powdery mildew (*Sphaerotheca pannosa*), rust (*P. disciflorum*), blackspot (*Diplocarpon rosae*), and *Botrytis* (*Botrytis cinerea*) diseases under normal growing conditions.

I claim:

1. A new and distinct variety of rose plant as herein illustrated and described.

* * * * *

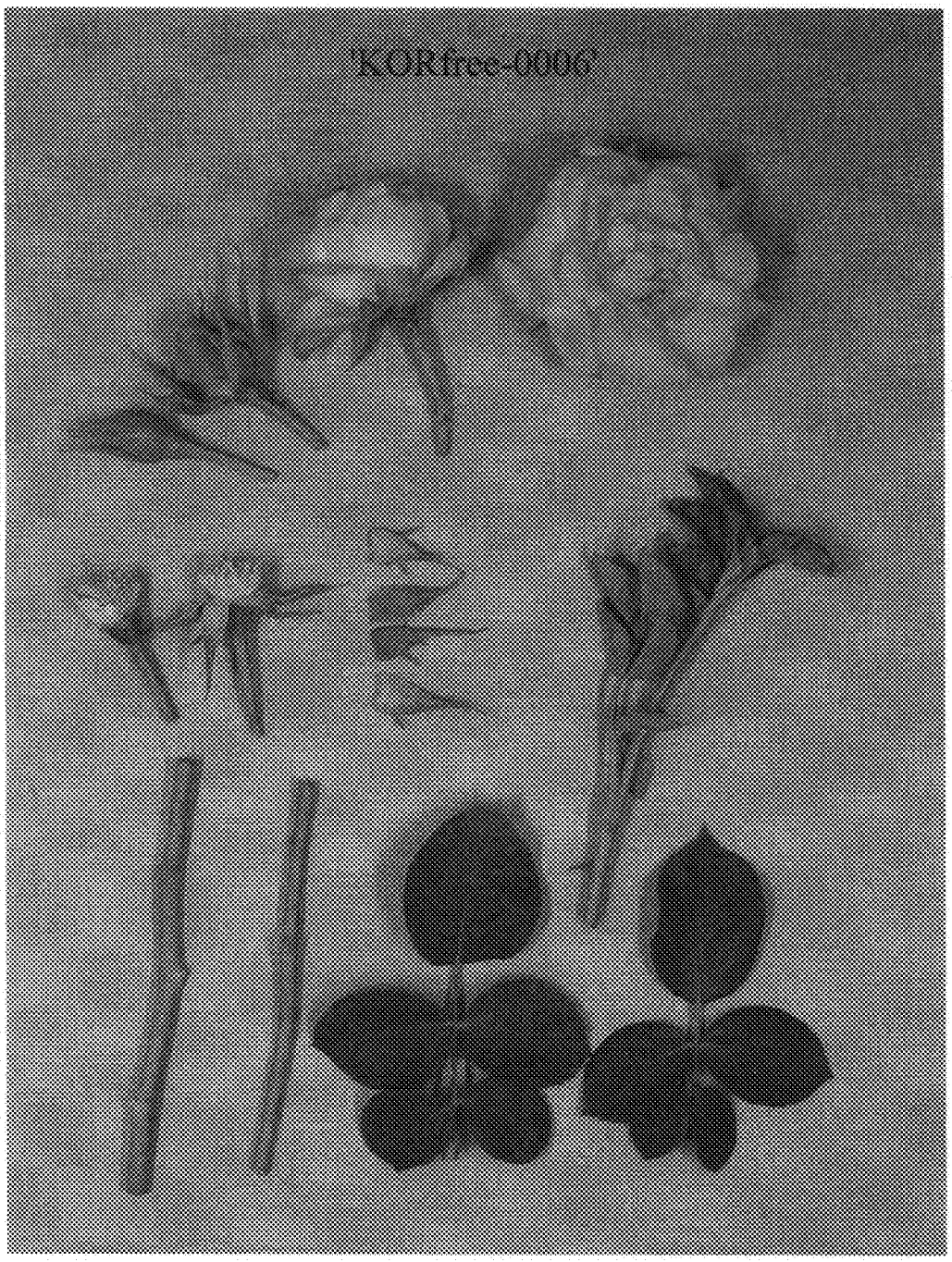
'KORfree-0006'